United States Patent

Heinze-Krauss et al.

[11] Patent Number: 5,925,632
[45] Date of Patent: Jul. 20, 1999

[54] DERIVATIVES OF 3-PYRROLIDYLIDENE-2-ONE-CEPHALSPORINES

[75] Inventors: Ingrid Heinze-Krauss, Schliengen; Hans Richter, Grenzach-Wyhlen, both of Germany

[73] Assignee: Hoffmann-La Roche Inc., Nutley, N.J.

[21] Appl. No.: 08/875,563

[22] PCT Filed: Feb. 16, 1996

[86] PCT No.: PCT/EP96/00667

§ 371 Date: Jul. 25, 1997

§ 102(e) Date: Jul. 25, 1997

[87] PCT Pub. No.: WO96/26943

PCT Pub. Date: Sep. 6, 1996

[30] Foreign Application Priority Data

Feb. 27, 1995 [DE] Germany .............................. 95102742

[51] Int. Cl.$^6$ ........................ C07D 501/56; A61K 31/545
[52] U.S. Cl. ........................................... 514/202; 540/222
[58] Field of Search .............................. 540/222; 514/202

[56] References Cited

U.S. PATENT DOCUMENTS 5,523,400 6/1996 Wei et al. ................................. 514/202

FOREIGN PATENT DOCUMENTS 620225 10/1994 European Pat. Off. .

Primary Examiner—Mark L. Berch
Attorney, Agent, or Firm—George W. Johnston; Patricia S. Rocha-Tramaloni; Alan P. Kass

[57] ABSTRACT

Compounds of formula (I)

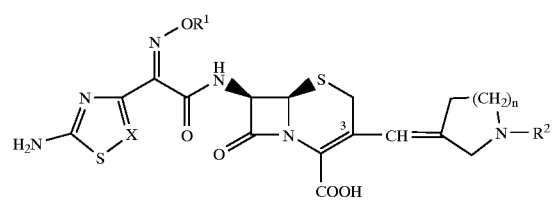

wherein $R^1$ is hydrogen, lower alkyl, aralkyl, cycloalkyl, $R^3CO$— or —$C(R^4R^5)CO_2R^6$; where $R^4$ and $R^5$ are each independently hydrogen or lower alkyl, or $R^4$ and $R^5$ taken together with the carbon atom to which they are attached form a cycloalkyl group; $R^3$ is hydrogen or lower alkyl and $R^6$ is hydrogen, lower alkyl, lower alkenyl or a carboxylic acid protecting group;

$R^2$ is isobutyl, 2,2-dimethyl-propyl or cyclohexyl-methyl;

n is 0, 1 or 2;

X is CH or N;

as well as readily hydrolyzable esters thereof, pharmaceutically acceptable salts of said compounds and hydrates of the compounds of formula I and of their esters and salts are disclosed. These compounds have valuable antibacterial activity.

10 Claims, No Drawings

DERIVATIVES OF 3-PYRROLIDYLIDENE-2-ONE-CEPHALSPORINES

This application is a 371 of PCT/EP96/00667 filed Feb. 16, 1996.

The present invention relates to cephalosporin derivatives of the general formula I

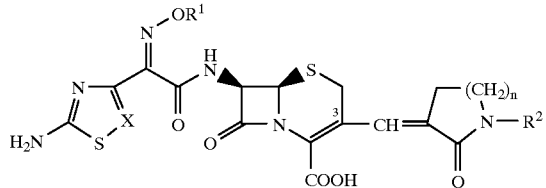

wherein

- $R^1$ is hydrogen, lower alkyl, aralkyl, cycloalkyl, $R^3CO—$ or $—C(R^4R^5)CO_2R^6$; where $R^4$ and $R^5$ are each independently hydrogen or lower alkyl, or $R^4$ and $R^5$ taken together form a cycloalkyl group; $R^3$ is hydrogen or lower alkyl and $R^6$ is hydrogen, lower alkyl, lower alkenyl or a carboxylic acid protecting group.
- $R^2$ is isobutyl, sec. butyl, 2,2-dimethyl-propyl, 2-ethyl-butyl, cyclobutyl-methyl, cyclopentyl-methyl or cyclohexyl-methyl;
- n is 0, 1 or 2;
- X is CH or N as well as readily hydrolyzable esters thereof, pharmaceutically acceptable salts of said compounds and hydrates of the compounds of formula I and of their esters and salts.

In above compounds of formula I the substituent in position 3 can be present in the E-form formula Ia or in the Z-form formula Ib

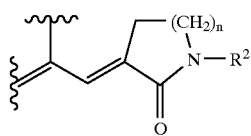

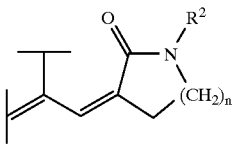

In a particular embodiment of the compounds of formula I n is 1. Moreover $R^1$ is preferably hydrogen or cyclopentyl. X is preferably CH. The compounds of the formula I are preferably in the Z-form at the oximino group and E-form for the substitutent in position 3.

Preferred compounds of formula I include:
(6R,7R-7-[(Z)-2-(2-amino-thiazol-4-yl)-2-hydroxyiminoacetylamino]-3-[(E)-1-isobutyl-2-oxo-pyrrolidin-3-ylidenemethyl]-8-oxo-5-thia-1-azabicyclo[4.2.0]oct-2-ene-2-carboxylic acid,

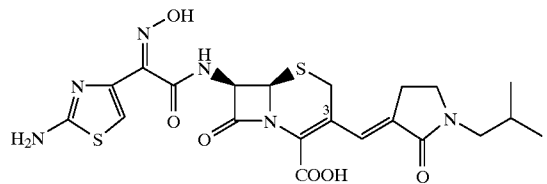

(6R,7R)-7-[(Z)-2-(2-amino-thiazol-4-yl)-2-(hydroxyiminoacetylamino]-3-[(E)-1-(2,2-dimethyl-propyl)-2-oxo-pyrrolidin-3-ylidenemethyl]-8-oxo-5-thia-1-azabicyclo[4.2.0]oct-2-ene-2-carboxylic acid and

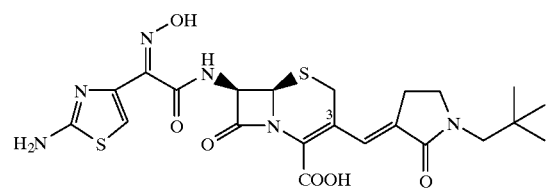

(6R,7R-7-[(Z)-2-(2-amino-thiazol-4-yl)2-(hydroxyiminoacetylamino]-3-[(E)-1-cyclohexylmethyl-2-oxo-pyrrolidin-3-ylidenemethyl]-8-oxo-5-thia-1-azabicyclo[4.2.0]oct-2-ene-2-carboxylic acid.

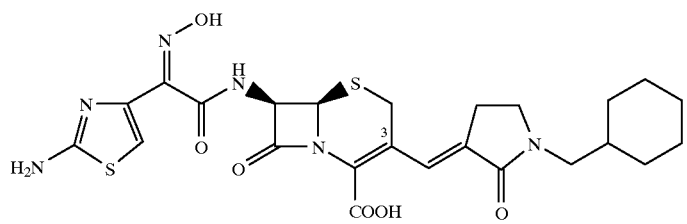

The invention also relates to pharmaceutical compositions and methods of use of the above.

As used herein, the term "lower alkyl" refers to both straight and branched chain saturated hydrocarbon groups having 1 to 8 and preferably 1 to 4 carbon atoms, for example, methyl, ethyl, n-propyl, isopropyl, tertiary butyl and the like.

By the term "aralkyl" is meant an alkyl group containing an aryl group. It is a hydrocarbon group having both aromatic and aliphatic structures, that is, a hydrocarbon group in which a lower alkyl hydrogen atom is substituted by a monocyclic aryl group, e.g., phenyl, tolyl, etc.

By the term "cycloalkyl" is meant a 3–7 membered saturated carbocyclic moiety, e.g., cyclopropyl, cyclobutyl, cyclohexyl, etc.

As used herein, "lower alkenyl" refers to unsubstituted or substituted hydrocarbon chain radicals having from 2 to 8 carbon atoms, preferably from 2 to 4 carbon atoms, and having at least one olefinic double bond, e.g. allyl, vinyl etc.

The term "carboxylic acid protecting group" refers to protecting groups conventionally used to replace the acidic proton of a carboxylic acid. Examples of such groups are benzyhydryl, t-butyl, p-nitrobenzyl, p-methoxybenzyl and allyl.

As used herein pharmaceutically acceptable salts useful in this invention include salts derived from metals, the ammonium salt, quaternary ammonium salts derived from organic bases and amino acid salts. Examples of preferred metal salts are those derived from the alkali metals, for example, lithium ($Li^+$), sodium ($Na^+$) and potassium ($K^+$), and from the alkaline earth metals, for example, calcium ($Ca^{++}$) and magnesium ($Mg^{++}$), although cationic forms of other metals, such as iron ($Fe^{++}$ or $Fe^{+++}$), aluminium ($Al^{+++}$), and zinc ($Zn^{++}$) are within the scope of this invention. Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like, etc. Those salts derived from amines include salts with N-ethyl-piperidine, procaine, dibenzylamine, N,N'-dibenzylethylenediamine, alkylamines or dialkylamines as well as salts with amino acids such as, for example, salts with arginine or lysine.

As readily hydrolyzable esters of the compounds of formula I there are to be understood compounds of formula I, the carboxy group(s) of which (for example, the 2-carboxy group) is/are present in the form of readily hydrolyzable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy] ethyl ester; 1-(acetyloxy) ethyl ester; (5-methyl-2-oxo-1,3-dioxol-4-yl) methyl ester; 1-[[(cyclohexyloxy)carbonyl]oxy] ethyl ester; and 3,3-dimethyl-2-oxobutyl ester. It will be appreciated by those of ordinary skill in the art that the readily hydrolyzable esters of the compounds of the present invention can be formed at a free carboxy group of the compound, for example, at the carboxy group in position 1 and at a carboxy group —$COOR^6$.

The compounds of formula I as well as their salts and readily hydrolyzable esters can be hydrated. The hydration can be effected in the course of the manufacturing process or can occur gradually as a result of hygroscopic properties of an initially anhydrous product.

The compounds of the present invention are useful as antibiotics having potent and broad antibacterial activity. They also possess good oral absorption properties.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositiories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

The compounds of formula I and their salts, or hydrates, can preferably be used for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectum by the agar dilution method in Mueller Hinton agar.

The following compounds were tested:

A: (6R,7R)-7-[(Z)-2-(2-amino-thiazol-4-yl)-2-hydroxyiminoacetylamino]-3-[(E)-1-isobutyl-2-oxo-pyrrolidin-3-ylidenemethyl]-8-oxo-5-thia-1-azabicyclo[4.2.0]oct-2-ene-2-carboxylic acid trifluoroacetate B: (6R,7R)-7-[(Z)-2-(2-amino-thiazol-4-yl)-2-(hydroxyiminoacetylamino]-3-[(E)-1-(2,2-dimethyl-propyl)-2-oxo-pyrrolidin-3-ylidenemethyl]-8-oxo-5-thia-1-azabicyclo[4.2.0]oct-2-ene-2-carboxylic acid trifluoroacetate and C: (6R,7R)-7-[(Z)-2-(2-amino-thiazol-4-yl)-2-(hydroxyiminoacetylamino]-3-[(E)-1-cyclohexylmethyl-2-oxo-pyrrolidin-3-ylidenemethyl]-8-oxo-5-thia-1-azabicyclo[4.2.0]oct-2-ene-2-carboxylic acid trifluoroacetate.

The antibacterial Spectrum appears below:
MIC: Minimum Inhibiting Concentration Values

| Antibacterial Spectrum (MIC, µg/ml) | | | | | |
|---|---|---|---|---|---|
| | A | B | C | Cefdinir | Ceftriaxone |
| S. aureus 6538 | 1 | 1 | 1 | 0.5 | 4 |
| S. aureus 734 MRSA | 4 | 16 | 8 | >32 | >32 |
| S. pyogenes B15 | ≦0.06 | ≦0.06 | ≦0.06 | ≦0.06 | ≦0.06 |
| S. pneumoniae Q19 | ≦0.06 | ≦0.06 | ≦0.06 | 0.25 | ≦0.06 |
| S. agalactiae QK44 | 0.25 | 0.5 | 0.25 | 0.25 | ≦0.06 |
| S. viridans group 016 | ≦0.06 | 1 | 0.5 | 2 | 0.25 |
| E. faecalis 6 | 1 | 2 | 2 | 8 | >32 |
| L. monocytogenes BK23 | 4 | 4 | 4 | 16 | >16 |
| H. influenzae 1 | | | | 0.5 | ≦0.06 |
| M. catarrhalis RA21 | 1 | 16 | 16 | 1 | 1 |
| N. meningitidis 69480 | | | | ≦0.06 | ≦0.01 |
| E. coli 25922 | 0.25 | 1 | 1 | 0.25 | ≦0.06 |
| K. pneumoniae 418 | 0.5 | 1 | 1 | 0.12 | ≦0.06 |
| E. cloacae 908SSi | 0.5 | 2 | 2 | 32 | 0.25 |
| E. cloacae 908R | 16 | 32 | 16 | >32 | >32 |
| C. freundii 902 | 0.25 | 1 | 1 | 16 | 0.25 |
| C. freundii 43 | 4 | 8 | 8 | >32 | 32 |
| P. mirabilis 2117 | 0.25 | 0.25 | 0.5 | 0.12 | ≦0.06 |
| P. vulgaris 1028 | | 4 | 0.5 | 1 | 0.12 |
| M. morganii 6H-137 | 0.25 | 0.5 | 4 | 8 | ≦0.06 |
| S. marcescens 69438 | 1 | 4 | 4 | 16 | 0.25 |
| P. aeruginosa 27853 | | | | >32 | 16 |
| X. maltophilia 1AC739 | >32 | >32 | >32 | >32 | >32 |
| Actinetobacter sp. 51-156 | 16 | 32 | 16 | >32 | 32 |

Cefdinir: [6R-[6a,7b(Z)]]-7-(2-Amino-4-thiazolyl)[(hydroxyimino)]acetyl]amino]-3-ethenyl-8-oxo-5-thia-1-azabicyclo-[4.2.0]oct-2-ene-2-carboxylic acid Ceftriaxone: [6R-[6a,7b(Z)]]-7-([[2-Amino-4-thiazolyl)(methoxyimino)acetyl]amino]-8-oxo-3-[[(1,2,5,6-tetrahydro-2-methyl-5,6dioxo-1,2,4-triazin-3-yl)thio]methyl]-5-thia-1-azabicyclo[4.2.0]oct-2-ene-2-carboxylic acid The compounds of the formula I in accordance with the invention as well as their pharmaceutical acceptable salts, hydrates, or readily hydrolyzable esters can be manufactured in accordance with the invention by (a) treating a compound having the formula II

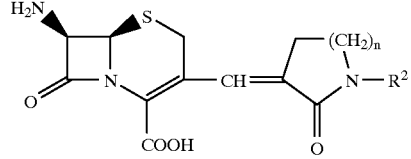

in which $R^2$ and n are defined above, or an ester or salt thereof, with a carboxylic acid of the general formula III

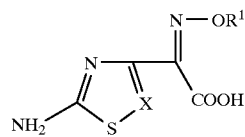

in which $R^1$ and X are defined above, or $R^1$ is a reactive functional derivative thereof, or (b) cleaving off the amino, hydroxy and/or carboxy protecting group in a compound having the formula IV

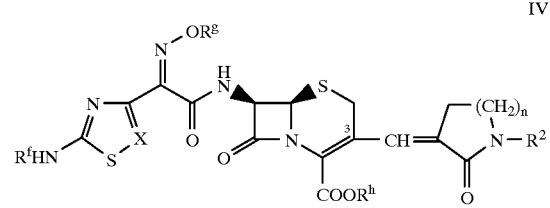

in which $R^2$ is defined above, $R^f$ is hydrogen or an amino protecting group, $R^g$ is hydrogen or a hydroxy protecting group, $R^h$ is hydrogen or a carboxy protecting group, provided that at least one of $R^f$, $R^g$ and $R^h$ is a corresponding protecting group or a salt thereof, or (c) for the manufacture of a readily hydrolyzable ester of a compound of formula I subjecting a carboxylic acid of formula I to a corresponding esterification, or (d) for the manufacture of salts or hydrates of a compound of formula I or hydrates of said salts converting a compound of formula I into a salt or hydrate or into a hydrate of said salts.

The reaction of compounds II and III or a reactive derivative of III according to embodiment (a) can be carried out in a manner known per se. The carboxy group in compounds II can be protected; for example, by esterification to form a readily cleavable ester such as a silyl ester (e.g. the trimethylsilyl ester) or benzhydryl ester. The carboxy group can also be protected in the form of one of the aforementioned readily hydrolyzable esters. Furthermore, the carboxy group can be protected by salt formation with an inorganic or tertiary organic base such as triethylamine. The amino group present in the acylating agent of formula III can be protected. Possible protecting groups are, for example, protecting groups which are cleavable by acid hydrolysis (e.g. the tert.-butoxycarbonyl or trityl groups) or by basic hydrolysis (e.g. the trifluoroacetyl group). Preferred protecting groups are the chloroacetyl, bromoacetyl and iodoacetyl groups, especially the chloroacetyl group. These last-mentioned protecting groups can be cleaved off by treatment with thiourea. The 7-amino group in compounds II can be protected, for example, by a silyl protecting group such as the trimethylsilyl group.

In reacting a 7-amino compound of formula II with a carboxylic acid of formula III or a reactive functional derivative thereof, for example, a free carboxylic acid can be reacted with an aforementioned ester of a compound of formula II in the presence of a carbodiimide such as dicyclohexylcarbodiimide in an inert solvent such as ethyl acetate, acetonitrile, dioxan, chloroform, methylene chloride, benzene or dimethylformamide, and subsequently the ester group can be cleaved off. Oxazolium salts (e.g. N-ethyl-5-phenyl-isoxazolium-3'-sulphonate) can be used in place of carbodiimides in the foregoing reaction.

According to another embodiment, a salt of an acid of formula II (e.g. a trialkylammonium salt such as the triethylammonium salt) is reacted with a reactive functional derivative of a carboxylic acid of formula III as mentioned earlier in an inert solvent (e.g. one of the aforementioned solvents).

According to a further embodiment, an acid halide, preferably the chloride, of a carboxylic acid of formula m is reacted with an amine of formula II. The reaction is preferably carried out in the presence of an acid-binding agent, for example in the presence of aqueous alkali, preferably sodium hydroxide, or in the presence of an alkali metal carbonate such as potassium carbonate or in the presence of a lower alkylamine such as triethylamine. As the solvent there is preferably used water, optionally in admixture with an inert organic solvent such as tetrahydrofuran or dioxan. The reaction can also be carried out in an aprotic organic solvent such as dimethylformamide, dimethylacetamide, dimethylsulphoxide or hexamethylphosphoric acid triamide. When a silylated compound of formula II is used, the reaction is carried out in an anhydrous medium.

Advantageous alternatives for acylation, where the amino group present in the acylating agent of formula III need not be protected, involves the use of a 2-benzothiazolyl thioester or a 1-hydroxybenzotriazole ester of the carboxylic acid. For instance, the 2-benzthiazolyl thioester may be reacted with the compound II in an inert organic solvent such as a chlorinated hydrocarbon e.g. methylene chloride, in acetone, ethyl acetate or in a mixture of such solvents with water. The 1-hydroxybenzotriazole ester can be employed by reacting the carboxylic acid with 1-hydroxybenzotriazole and a carbodiimide, especially N,N'-dicyclohexylcarbodiimide or N,N'-diisopropylcarbodiimide in an inert organic solvent, preferably methylene chloride, dimethylformamide, tetrahydrofuran, acetonitrile or ethyl acetate.

The reaction of a 7-amino compond of formula II with the carboxylic acidof formula III or a reactive derivative thereof can conveniently be carried out at a temperature between about −40° C. and +60° C., e.g. at room temperature.

Embodiment (b) of the process of the present invention involves deprotection (removal) of protected amino, hydroxy or carboxylic groups present in a compound of formula IV and can be carried and as follows:

Removal of amino protecting groups

Possible amino-protecting groups are those employed in peptide chemistry, such as an alkoxycarbonyl group, e.g., t-butoxycarbonyl, etc., a substituted alkoxycarbonyl group, e.g., trichloroethoxycarbonyl etc., an optionally substituted aralkyloxycarbonyl group, e.g., p-nitrobenzyloxycarbonyl or benzyloxycarbonyl, an aralkyl group such as trityl or benzhydryl or a halogen-alkanoyl group such as chloroacetyl, bromoacetyl, iodoacetyl or trifluoroacetyl. Preferred protecting groups are t-butoxycarbonyl (t-BOC) and trityl.

The amino protecting groups may be cleaved off by acid hydrolysis (e.g. the t-butoxycarbonyl or trityl group), e.g. aqueous formic acid, or by basic hydrolysis (e.g. the trifluoroacetyl group). The chloroacetyl, bromoacetyl and iodoacetyl groups are cleaved off by treatment with thiourea.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C.–30° C.

Removal of hydroxy protecting groups

Possible hydroxy protecting groups are such as are commonly known in the art, e.g.

for protection of hydroxyimino groups ($R^1$=hydrogen in compounds of formula I), usually trityl, lower alkanoyl, preferably acetyl, tetrahydropyranyl protecting groups are employed These protecting groups are e.g. removed as follows:

trityl in acidic solvents like 90% formic acid at about 0 to 50° C. or triethylsilane in trifluoroacetic acid at about −20 to 25° C.; in organic solutions of hydrochloric acid at about −50 to 25° C.;

acetyl with weak inorganic bases like sodium bicarbonate in ethanol/water at about 0 to 50° C.;

tetrahydropyranyl with weak organic acids like p-toluenesulfonic acid in an alcohol, e.g. ethanol, at about 0° C. to the boiling point of the mixture;

Removal of protecting groups at the carboxy function

As ester protecting groups one may utilize an ester form which can be easily converted into a free carboxyl group under mild conditions, the ester protecting group being exemplified by, for example, t-butyl, p-nitrobenzyl, p-methoxybenzyl, benzhydryl, allyl, etc.

These protecting groups may be removed as follows:

benzhydryl trifluoroacetic acid with anisol, phenol, cresol or triethylsilane at about −40° C. to room temperature; hydrogen with Pd/C in an alcohol such as ethanol or in tetrahydrofuran; $BF_3$-etherate in acetic acid at about 0 to 50° C.;

t-butyl formic acid or trifluoroacetic acid with or without anisol, phenol, cresol or triethylsilane and a solvent such as dichloromethane at about −10° C. to room temperature;

p-nitrobenzyl sodium sulfide in acetone/water at about 0 to room temperature; or hydrogen with Pd/C in an alcohol such as ethanol or in tetrahydrofuran;

p-methoxybenzyl formic acid at about 0 to 50° C.; or trifluoroacetic acid and anisol, phenol or triethylsilane at about −40° C. to room temperature;

allyl palladium(O) catalyzed transalkylation reaction in the presence of sodium or potassium salt of 2-ethyl hexanoic acid, see for example J. Org. Chem. 1982, 47, 587.

In order to manufacture a readily hydrolyzable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0–40° C.

The manufacture of the salts and hydrates of the compounds of formula I or the hydrates of said salts in accordance with embodiment (d) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like).

Correspondingly, salt formation is brought about by the addition of an organic or inorganic salt. The temperature at which the salt formation is carried out is not critical. The salt formation is generally carried out at room temperature, but it can be carried out at a temperature slightly above or below room temperature, for example in the range of 0° C. to +50° C.

The manufacture of the hydrates usually takes place automatically in the course of the manufacturing process or as a result of the hygroscopic properties of an initially anhydrous product. For the controlled manufacture of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1

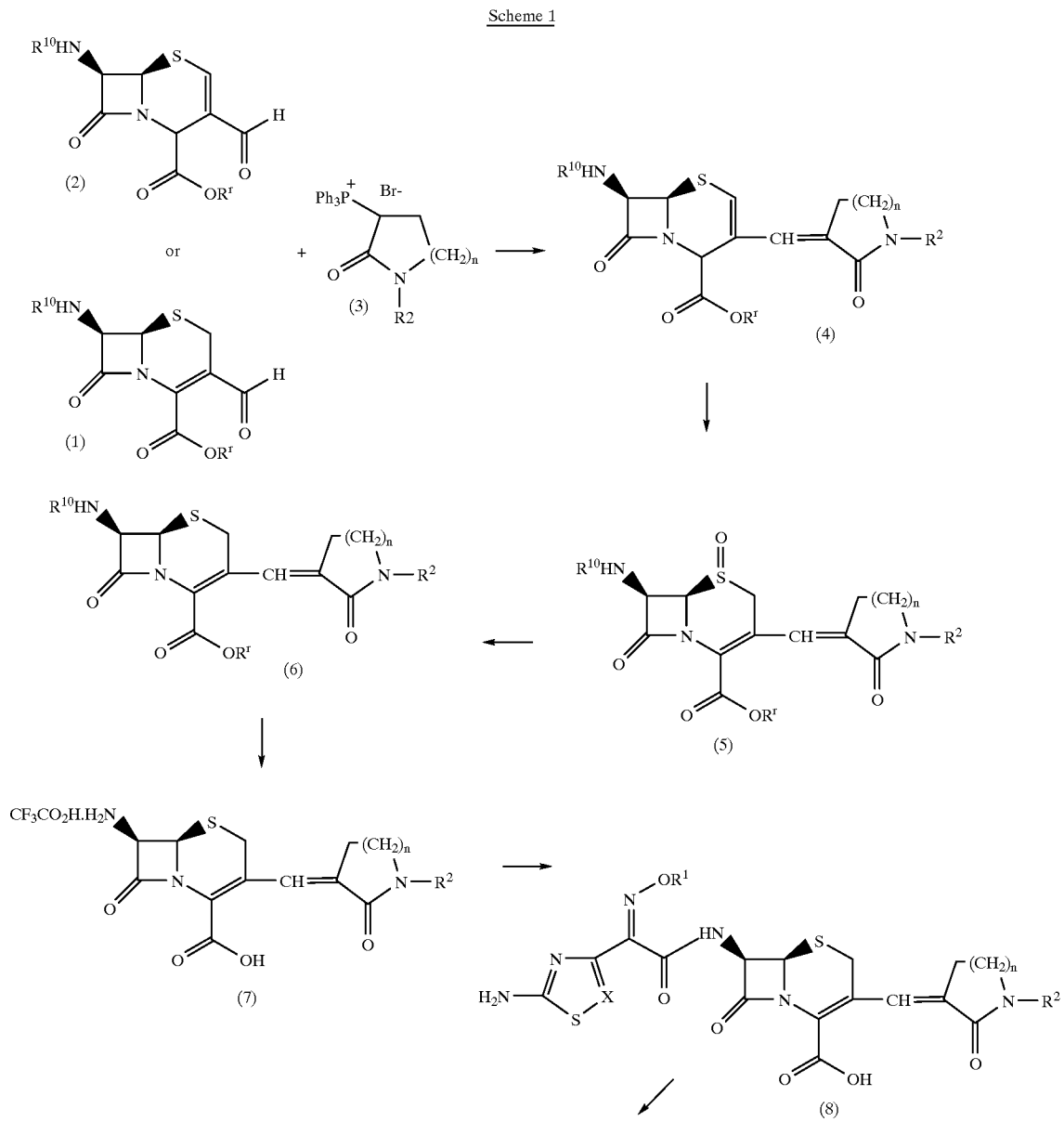

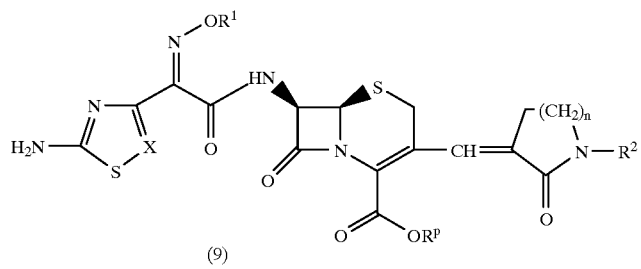

(9)

Scheme 1

1 or 2+3→4

The reaction of known 2-cephem aldehyde (1) or 3-cephem aldehyde (2) where $R^r$ is a carboxy protecting group as defined under $R^h$ above and $R^{10}$ is a amino protecting group with a Wittig reagent, exemplified by structure 3, yield the coupling product 4. The reaction is carried out in the presence of a base which is either an inorganic base (sodium or potassium hydroxide, sodium or potassium carbonate etc.), an organic base (tertiary amines), an organolithium such as butyl lithium or phenyllithium or an epoxide such as 1,2-butyleneoxide The preferred solvents, in the case of inorganic base being used, are water and water-miscible solvent (acetone, tetrahydrofuran, or alcohols etc.); in the case organic base being used, an inert solvent such as methylene chloride, chloroform, benzene, tetrahydrofuran; in the case of organolithium being used, benzene or tetrahydrofuran; and in the case an epoxide being used, the epoxide itself (e.g. 1,2-butyleneoxide). The temperature for the reaction ranges from −20° C. to 80° C. The preferred conditions are exemplified in the examples.

In the normal Wittig Reaction according to scheme 1, the E isomer is the predominant product. Invariably, less than 10% Z-isomer is formed, the amount depending on the reagents and conditions.

4→5

Compound 4 is converted to the sulfoxide 5 with an oxidizing agent which can be hydrogen peroxide or a peracid, preferably m-chloroperbenzoic acid. The temperature ranges from −20° C. to room temperature and any suitable solvent, preferably chlorinated hydrocarbon or benzene can be used.

5→6

The de-oxygenation of the sulfoxide 5 is carried out in the presence of phosphorus tribromide in dimethylformamide or in the mixed solvent of dimethylformamide and N-methylacetamide. The reaction temperature for the reaction is from about −40 to about 0° C.

6→7

The protecting groups $R^r$ and $R^{10}$ are removed and the reaction condition used are depending on the nature of the protecting groups. In the case of $R^{10}$ being t-butoxycarbonyl and $R^r$ being benzhydryl, trifluoroacetic acid is employed, at temperature of about −20° C. to about room temperature (about 22° C.).

7→8

The acylation of compound 7 can be carried out with an organic acid which is activated with known reagents, preferably thionyl chloride, oxalyl chloride, dicyclohexylcarbodiimide, bis-[benzthiazolyl-(2)]disulfide, N-hydroxy benzotriazole or a 2-halo N-methylpyridinium salt. The reaction is carried out with or without the base (inorganic or organic bases) depending on the method activation and a wide range of solvents, from water and water-miscible solvent to inert solvents such as chloroform, dimethylformamide (DMF) or dimethyl-sulfoxide (DMSO) can be used. The $R^1$ group, if necessary, can be further deprotected with a reaction condition suitable for the removal of the protecting group.

8→9

The 2-carboxylic finction of compound 8 is converted to the prodrug esters which are readily hydrolyzable in vivo. $R^p$ can be any such esters known in the art by esterification with the corresponding alcohol of $R^p$ or by treating with the corresponding halide of RP and a base; the preferred esters are exemplified in the examples. The $R^1$ group, if necessary, can be further deprotected with a reaction condition suitable for the removal of the protecting group.

Scheme 2

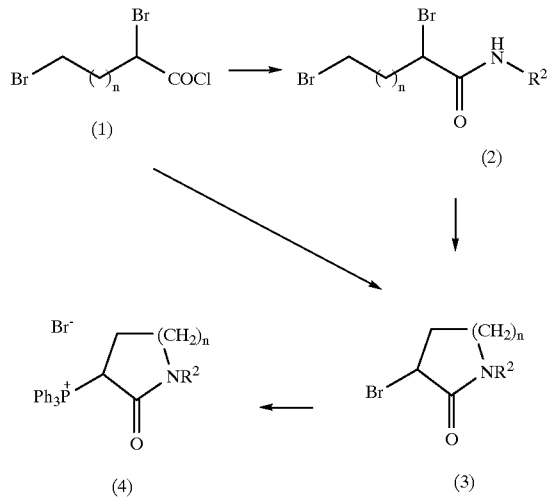

n=1 or 2

$R^2$=as defined above

Ph=phenyl The processes in scheme 2 are carried out as follows:

1 to 2

The known dibromo acid chlorides (1, n=1, 2) can be converted to the amides (2) using the appropriate amines or aminehydrohalides and inorganic bases such as sodium or potassium hydroxide, sodium or potassium carbonate etc., organic bases such as sodium methoxide or tertiary amines such as triethylamine, diisopropylethylamine etc. The reaction is carried out in biphasic solvent mixtures like water/dichloromethane or water/chloroform etc., when inorganic bases are used. In case of organic bases or tertiary amines being used an inert solvent such as methylene chloride, chloroform, benzene, tetrahydrofuran etc. is preferred. The reaction-temperatures range from −10 to 100° C.

2 to 3

Cyclization of the N-substituted dibromoamides (2) can be accomplished under the usual phase transfer catalytic conditions using catalysts like Dowex 2×10, tetraalkylammonium salts, tetraalkylarylammonium salts, crown ethers etc. with bases like aqueous sodium or potassium hydroxide, sodium or potassium carbonate etc.

Alternatively, strong bases like sodium hydride, lithium diisopropylamide, potassium t-butoxide can be used in solvents like tetrahydrofuran, dichloromethane, dimethoxyethane or diethylether at reaction temperatures between −78 and +80° C.

1 to 3

The direct conversion of the acid chlorides into the bromolactams is possible when the first step (1 to 2) is carried out in biphasic solvent mixtures like water/dichloromethane or water/chloroform etc. together with sodium or potassium hydroxide as base. A catalyst like Dowex 2×10, tetralkylammonium salts, tetraalkylarylammonium salts, crown ethers etc. is added when the amid (2) has formed according to TLC or HPLC analysis. The temperatures range between 0 and 50° C.

3 to 4

The triphenylphosphonium salts (4) can be prepared by treating the bromolactams with triphenylphosphine in solvents like tetrahydrofuran, toluene, benzene, ethylacetate, dichloromethane, dichloroethane, chloroform et at temperatures between 0 and 150° C.

EXAMPLE 1

(a) rac-2,4-Dibromo-N-isobutyl-butyramide 1.52 g (20.8 mmol) Isobutylamine were dissolved in 3 ml of water, and 13 ml dichloromethane were added. The mixture was cooled to 0° C. and vigorously stirred. A solution of 5.0 g (18.9 mmol) of 2,4-dibromobutanoic acid chloride (J. Med. Chem., 1987, 30, 1995) in 3 ml dichloromethane was added within 5 min. Thereafter a solution of 0.83 g (20.8 mmol) NaOH in 1.5 ml water was added a a rate resulting in the temperature remaining between 7 and 10° C. After complete addition, stirring was continued for 3 h at this temperature. Finally the phases were separated and the aqueous phase was extracted thrice with 15 ml dichloromethane. The combined organic phases were washed once with 17 ml 0.5M HCl, once with 14 ml 5% sodium bicarbonate solution and once with 10 ml brine and dried over magnesium sulfate. After evaporation of the solvent a colourless solid was obtained.

Yield: 4.5 g (78.9%)
IR (Film): 3310, 1654, 1552 $cm^{-1}$
MS (EI): 299 (M)

(b) rac-3-Bromo-1-isobutyl-pyrrolidine-2-one 4.48 g (14.9 mmol) rac-2,4-Dibromo-N-isobutyl-butyramide were dissolved in 40 ml dichloromethane, then 17.3 ml of 50% sodium hydroxide solution and 0.48 g Dowex 2×10 were added. The mixture was stirred vigorously for 4 h at room temperature. Afterwards the mixture was poured into 50 ml ice/water an the phases were separated. The aqueous phase was extracted thrice with 20 ml dichloromethane, and the combined organic phases were washed once with 20 ml water, once with 20 ml brine and dried over magnesium sulfate. After evaporation of the solvent, the resulting colourless oil was chromatographed or silica gel (0.040–0.063 mm) with ethyl acetate/n-hexane 1:1 as eluent.

Yield: 2.74 g (83%) beige crystals
IR(KBr): 2960, 1694 $cm^{-1}$
MS(EI): 219 (M)

(c) rac-(1-Isobutyl-2-oxo-pyrrolidin-3-yl)-triphenylphosphonium bromide 2.74 g (12.4 mmol) rac-3-Bromo-1-isobutyl-pyrrolidine-2-one were dissolved in 12 ml THF, and 3.43 g (13.1 mmol) triphenylphosphine were added. The mixture was then refluxed for 3 days under argon atmosphere. After cooling to room temperature, the suspension was filtered with suction, the white crystals were washed with ice-cold THF and then dried under high vacuum.

Yield: 4.8 g (80%)
IR(KBr): 2768, 1683, 1436 $cm^{-1}$
MS(ISP): 402.4 ($M^+$)

(d) (E)-(2R,6R,7R)-7-tert-Butoxycarbonylamino-3-(1-isobutyl-2-oxo-pyrrolidin-3-ylidenemethyl)-8-oxo-5-thia-1-aza-bicyclo[4.2.0]oct-3-ene-2-carboxylic acid benzhydryl ester The suspension of 20.3 g (41.1 mmol) [6R-(6a,7b)]-7-[[(1,1-dimethylethoxy)carbonyl]amino]-3-formyl-8-oxo-5-thia-1-azabicyclo[4.2.0]oct-3-ene-2-carboxylic acid diphenylmethyl ester and 23.8 g (49.3 mmol) rac-(1-isobutyl-2-oxo-pyrrolidin-3-yl)-triphenyl-phosphonium bromide in 160 ml 1,2-butylene oxide was refluxed for 2 h. After cooling to room temperature the solvent was removed under reduced pressure and the residue was chromatographed on silica gel (0.040–0.063 mm) with ethyl acetate/n-hexane 1:1 as eluent. The product was then recrystallized from $CH_2Cl_2$/n-hexane.

Yield: 26.5 g (86.3%) white powder
IR(KBr): 1781, 1742, 1712, 1680 $cm^{-1}$
MS(ISP): 618.4($M+H^+$)
Microanalysis: $C_{34}H_{39}N_3O_6S$

|  | C | H | N | S |
|---|---|---|---|---|
| calc | 66.11 | 6.36 | 6.80 | 5.19 |
| calc.#) | 63.28 | 6.15 | 6.43 | 4.91 |
| found | 63.25 | 6.18 | 6.36 | 5.12 |

)corr. values with 0.42 mol $CH_2Cl_2$ (e) (E)-(5R,6R,7R)- and (5S,6R,7R)-7-tert-butoxycarbonylamino-3-(1-isobutyl-2-oxo-pyrrolidin-3-ylidenemethyl)-5,8-dioxo-5-thia-1-aza-bicyclo[4.2.0]oct-2-ene-2-carboxylic acid benzhydryl ester The solution of 11.3 g (18.3 mmol) (E)-(2R,6R,7R)-7-tert-butoxycarbonylamino-3-(1-isobutyl-2-oxo-pyrrolidin-3-ylidenemethyl)-8-oxo-5-thia-1-aza-bicyclo[4.2.0]oct-3-ene-2-carboxylic acid benzhydryl ester in 100 ml dichloromethane was cooled to 0° C. and treated dropwise with a solution of 4.5 g (18.3 mmol) m-chloroperoxybenzoic acid (70–75%) in 80 ml dichloromethane while keeping the temperature below 40° C. After stirring for an additonal hour a this temperature, 50 ml of a 10% aqueous sodium thiosulfate solution was added and the phases were separated. The aqueous phase was extracted thrice with 50 ml dichloromethane and the combined organic extractions were washed successively with aqueous solutions of 10% sodium thiosulfate and saturated sodium bicarbonate and finally water. After drying over magnesium sulfate the drying agent and solvent were removed, and the residue was purified by flash silica gel chromatography (0.040–0.063 mm, ethyl acetate/n-hexane 3:1), yielding the desired product as a yellow oil.

Yield: 10.2 g (87.8%)
IR(KBr): 1796, 1722, 1685 cm$^{-1}$
MS: 634.4 (M+H$^+$)

(f) (E)-(6R,7R)-7-tert-Butoxycarbonylamino-3-(1-isobutyl-2-oxo-pyrrolidin-3-ylidenemethyl)-8-oxo-5-thia-1-aza-bicyclo[4.2.0]oct-2-ene-2-carboxylic acid benzhydryl ester A solution of 22.7 g (35.8 mmol) (E)-(5R,6R,7R)- and (5S,6R,7R)-7-tert-butoxycarbonylamino-3-(1-isobutyl-2-oxo-pyrrolidin-3-ylidenemethyl)-5,8-dioxo-5-thia-1-aza-bicyclo[4.2.0]oct-2-ene-2-carboxylic acid benzhydryl ester in dichloromethane (230 ml), N-methyl acetamide (32 ml) and N,N-dimethyl formamide (34 ml) was cooled to –30° C. and treated with 13.6 ml (143 mmol) of phosphorus tribromide in dichloromethane (35 ml), while maintaining the temperature below –25° C. The solution was stirred for 1 hour at this temperature and then poured into a stirred solution of ice water (1 l) and dichloromethane (650 ml). The aqueous layer was separated and reextracted thrice with dichloromethane (250 ml each). The combined organic extractions were washed with an aqueous solution of saturated sodium bicarbonate, water and finally brine. After drying over magnesium sulfate, filtration and evaporation of the solvent, the residue was crystallized from dichloromethane/n-hexane to give the desired compound as a white powder.

Yield: 22.9 g (99.1%)
IR(KBr): 1786, 1721, 1685 cm$^{-1}$
MS: 618.4 (M+H$^+$)

(g) (E)-(6R,7R)-7-Amino-3-(1-isobutyl-2-oxo-pyrrolidin-3-ylidenemethyl)-8-oxo-5-thia-1-aza-bicyclo[4.2.0]oct-2-ene-2-carboxylic acid trifluoroacetate (E)-(6R,7R)-7-tert-Butoxycarbonylamino-3-(1-isobutyl-2-oxo-pyrrolidin-3-ylidenemethyl)-8-oxo-5-thia-1-aza-bicyclo[4.2.0]oct-2-ene-2-carboxylic acid benzhydryl ester (21.9 g, 35.0 mmol) was dissolved in 240 ml dichloromethane and 23 ml anisole. At 20° C. 120 ml trifluoroacetic acid were added dropwise while maintaining the temperature below 50° C. After complete addition the ice-bath was removed and the solution was stirred at ambient temperature for 2.5 hours The volatile material was then removed under reduced pressure and the remaining yellow oil was added slowly to 400 ml of diethyl ether, in which the product started to precipitate. After 1.5 hours the suspension was filtered under argon atmosphere and the remaining crystals were stirred in 150 ml of ethyl acetate for 2 hours. The suspension was filtered under argon giving the desired product as a yellow crystalline powder.

Yield: 11.2 g (74.5%)
IR(KBr): 1782, 1680, 1623 cm$^{-1}$

MS(ISP): 352.3 (M+H$^+$)
Microanalysis: $C_{18}H_{22}F_3N_3O_6S$

|  | C | H | N | S | F |
|---|---|---|---|---|---|
| calc | 46.45 | 4.76 | 9.03 | 6.89 | 12.25 |
| calc.#) | 51.52 | 5.54 | 10.83 | 8.26 | 4.70 |
| found | 50.93 | 5.57 | 10.53 | 8.13 | 4.31 |

)corr. values with 0.32 mol CF$_3$COOH

(h) (6R,7R)-7-[(Z)-2-(2-Amino-thiazol-4-yl)-2-trityloxyimino-acetylamino]-3-[(E)-1-isobutyl-2-oxo-pyrrolidin-3-ylidenemethyl]-8-oxo-5-thia-1-aza-bicyclo[4.2.0]oct-2-ene-2-carboxylic acid 482 mg (1.26 mmol) (E)-(6R,7R)-7-Amino-3-(1-isobutyl-2-oxo-pyrrolidin-3-ylidenemethyl)-8-oxo-5-thia-1-aza-bicyclo[4.2.0]oct-2-ene-2-carboxylic acid trifluoroacetate was suspended in dimethylformamide (21 ml) and stirred for 1 at room temperature. During this time a solution was formed to which 765 mg (1.39 mmol) of 2-(2-aminothiazol-4-yl)-(Z)-2-trityloxyimino-acetic acid 1-benzotriazole ester were added and the reaction mixture was stirred for 24 hours at room temperature. The solvent was removed under reduced pressure and the remainining residue was taken up in ethyl acetate. The solution was washed twice with water followed by brine and dried over magnesium sulfate. After filtration and evaporation of the solvent the semi-solid residue was treated with 50 ml diethyl ether and stirred for 30 min. The solid was filtered, washed with diethyl ether and n-hexane and dried under high vacuum.

Yield: 610 mg (64.5%)
IR(KBr): 1784, 1675, 1626 cm$^{-1}$
MS(ISP): 763.2 (M+H$^+$)

(i) (6R,7R)-7-[(Z)-2-(2-Amino-thiazol-4-yl)-2-hydroxyimino-acetylamino]-3-[(E)-1-isobutyl-2-oxo-pyrrolidin-3-ylidenemethyl]-8-oxo-5-thia-1-aza-bicyclo[4.2.0]oct-2-ene-2-carboxylic acid trifluoroacetate 16.8 ml (219.4 mmol) Trifluoroacetic acid was cooled to 0° C., and 2.0 g (2.62 mmol) (6R,7R)-7-[(Z)-2-(2-amino-thiazol-4-yl)-2-trityloxyimino-acetylamino]-3-[(E)-1-isobutyl-2-oxo-pyrrolidin-3-ylidenemethyl]-8-oxo-5-thia-1-aza-bicyclo[4.2.0]oct-2-ene-2-carboxylic acid were added portionwise, keeping the temperature below 5° C. After 5 min. at that temperature, 0.96 ml (6.06 mmol) of triethylsilane were added dropwise and the reaction mixture was stirred for 1 h at 0° C. During this time a beige suspension was formed which was poured with stirring into 100 ml of diethyl ether. After 1 h the crystals were collected by filtration and retreated with 50 ml diethyl ether. After 1.5 hours the product was filtered and dried under high vacuum.

Yield: 1.17 g (86%) beige crystalline powder
IR(KBr): 1778, 1670, 1633 cm–1
MS(ISP): 521.3 (M+H$^+$)
Microanalysis: $C_{21}H_{24}N_6O_6S_2$

|      | C     | H    | N     | S     | F    |
|------|-------|------|-------|-------|------|
| calc | 48.45 | 4.65 | 16.14 | 12.32 | 0.00 |
| calc.#) | 45.35 | 4.22 | 14.32 | 10.92 | 5.65 |
| found##) | 45.24 | 4.46 | 14.33 | 10.75 | 5.59 |

)corr. values with 0.58 mol CF$_3$COOH
)corr. values with 2.0% H$_2$O

(j) (6R,7R)-7-[(Z)-2-(2-Amino-thiazol-4-yl)-2-cyclopentyloxyimino-acetylamino]-3-[(E)-1-isobutyl-2-oxo-pyrrolidin-3-ylidenemethyl]-8-oxo-5-thia-1-aza-bicyclo[4.2.0]oct-2-ene-2-carboxylic acid A suspension of 3.0 g (7.70 mmol) (E)-(6R,7R)-7-amino-3-(1-isobutyl-2-oxo-pyrrolidin-3-ylidenemethyl)-8-oxo-5-thia-1-aza-bicyclo[4.2.0]oct-2-ene-2-carboxylic acid trifluoroacetate in 125 ml of dimethylformamide was stirred for 50 min. at room temperature. During this time most of the starting material dissolved. Then 3.47 g (8.58 mmol) (Z)-2-(2-amino-thiazol-4-yl)-2-cyclopentyloxyimino-thioacetic acid 5-benzothiazol-2-yl ester were added and the reaction mixture was stirred for 18 hours. The solvent was removed under reduced pressure, the crystals were collected by filtration and digerated in 25 ml ethyl acetate for 1 h, and 100 ml diethyl ether for 1.5 hours.

Yield: 2.92 g (60.8%) beige crystals
IR(KBr): 1783, 1676, 1629 cm$^{-1}$
MS(ISP): 589.4 (M+H$^+$)
Microanalysis: C$_{26}$H$_{32}$N$_6$O$_6$S$_2$

|      | C     | H    | N     | S     |
|------|-------|------|-------|-------|
| calc. | 53.05 | 5.48 | 14.28 | 10.89 |
| found#) | 52.18 | 5.50 | 14.04 | 10.74 |

)corr. values with 1.29% H$_2$O

EXAMPLE 2

(a) rac-2,4-Dibromo-N-(2,2-dimethyl-propyl)-butyramide

In analogy to 1(a), rac-2,4-dibromo-N-(2,2-dimethyl-propyl)-butyramide was synthesized from 10 g (0.115 mol) neopentylamine and 27.6 g (0.104 mol) 2,4-dibromo butanoic acid chloride.

Yield: 32.4 g (98.5%) colourless powder
IR(KBr): 3302, 1656, 1566 cm$^{-1}$
MS(EI): 298 (M-CH$_3$)

(b) rac-3-Bromo-1-(2,2-dimethyl-propyl)-pyrrolidine-2-one

In analogy to 1(b), rac-3-bromo-1-(2,2-dimethyl-propyl)-pyrrolidine-2-one was synthesized by cyclisation of 64.5 g (0.205 mol) rac-2,4-dibromo-N-(2,2-dimethyl-propyl)-butyramide.

Yield: 30.9 g (64.5%) white powder
IR(KBr): 1693, 1413 cm$^{-1}$
MS(ISP): 218 (M-CH$_3$)

(c) rac-[1-(2,2-Dimethyl-propyl)-2-oxo-pyrrolidin-3-yl]-triphenyl-phosphonium bromide In analogy to 1(c), rac-[1-(2,2-dimethyl-propyl)-2-oxo-pyrrolidin-3-yl]-triphenyl-phosphonium bromide was synthesized from 16.1 g (68.7 mm ol) rac-bromo-1-(2,2-dimethyl-propyl)-pyrrolidine-2-one and 19.8 g (75.6 mmol) of triphenylphosphine.

Yield: 31.5 g (92.2%) colourless powder
IR(KBr): 2776, 1684, 1482 cm$^{-1}$
MS(ISP): 416.4 (M$^+$)

(d) (E)-(2R,6R,7R)-7-tert-Butoxycarbonylamino-3-[1-(2,2-dimethyl-propyl)-2-oxo-pyrrolidin-3-ylidenemethyl]-8-oxo-5-thia-1-aza-bicyclo[4.2.0]oct-3-ene-2-carboxylic acid benzhydryl ester In analogy to 1(d), (E)-(2R,6R,7R)-7-tert-butoxycarbonylamino-3-[1-(2,2-dimethyl-propyl)-2-oxo-pyrrolidin-3-ylidenemethyl]-8-oxo-5-thia-1-aza-bicyclo[4.2.0]oct-3-ene-2-carboxylic acid benzhydryl ester was synthesized from 30.6 g (61.6 mmol) rac-[1-(2,2-dimethyl-propyl)-2-oxo-pyrrolidin-3-yl]-triphenyl-phosphonium bromide and 25.4 g (51.3 mmol) [6R-(6a,7b)]-7-[[(1,1-dimethylethoxy)carbonyl]amino]-3-formyl-8-oxo-5-thia-1-azabicyclo[4.2.0]oct-3-ene-2-carboxylic acid diphenylmethyl ester.

Yield: 18.2 g (56.0%) yellow foam
IR(KBr): 1783, 1743, 1718 cm$^{-1}$
MS(ISP): 632.4 (M+H$^+$)

(e) (E)-(5R,6R,7R)- and (5S,6R,7R)-7-tert-butoxycarbonylamino-3-[1-(2,2-dimethyl-propyl)-2-oxo-pyrrolidin-3-ylidenemethyl]-5,8-dioxo-5-thia-1-aza-bicyclo[4.2.0]oct-2-ene-2-carboxylic acid benzhydryl ester In analogy to 1(e), (E)-(5R,6R,7R)- and (5S,6R,7R)-7-tert-butoxycarbonylamino-3-[1-(2,2-dimethyl-propyl)-2-oxo-pyrrolidin-3-ylidenemethyl]-5,8-dioxo-5-thia-1-aza-bicyclo[4.2.0]oct-2-ene-2-carboxylic acid benzhydryl ester were synthesized from 18.2 g (28.8 mmol) (E)-(2R,6R,7R)-7-tert-butoxycarbonylamino-3-[1-(2,2-dimethyl-propyl)-2-oxo-pyrrolidin-3-ylidenemethyl]-8-oxo-5-thia-1-aza-bicyclo[4.2.0]oct-3-ene-2-carboxylic acid benzhydryl ester and 7.1 g (28.8 mmol) m-chloroperoxybenzoic acid (70–75%).

Yield: 12.0 g (64.3%) yellow foam
IR(KBr): 1798, 1723, 1689 cm$^{-1}$
MS(ISP): 648.3 (M+H$^+$)

(f) (E)-(6R,7R)-7-tert-Butoxycarbonylamino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid benzhydryl ester In analogy to 1(f), (E)-(6R,7R)-7-tert-butoxycarbonylamino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid benzhydryl ester was synthesized from 12.0 g (0.185 mol) (E)-(5R,6R,7R)- and (5S,6R,7R)-7-tert-butoxycarbonylamino-3-[1-(2,2-dimethyl-propyl)-2-oxo-pyrrolidin-3-ylidenemethyl]-5,8-dioxo-5-thia-1-aza-bicyclo[4.2.0]oct-2-ene-2-carboxylic acid benzhydryl ester by reduction with 20.1 g (0.74 mol) phosphorus tribromide.

Yield: 9.5 g (82.9%) pale yellow powder.
IR(KBr): 1786, 1721, 1692 cm$^{-1}$
MS(ISP): 632.4 (M+H$^+$)

(g) (E)-(6R,7R)-7-Amino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid trifluoroacetate In analogy to 1(g), (E)-(6R,7R)-7-amino-3-[1-(2,2-dimethyl-propyl)-2-oxo-pyrrolidin-3-ylidenemethyl]-8- oxo-5-thia-1-aza-bicyclo[4.2.0]oct-2-ene-2-carboxylic acid trifluoroacetate was synthesized by deprotection of 9.50 g (0.15 mol) (E)-(6R,7R)-7-tert-butoxycarbonylamino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid benzhydryl ester in 48.5 ml (0.63 mol) trifluoroacetic acid and 10 ml anisole.

Yield: 4.7 g (85.4%) brownish powder
IR(KBr): 1783, 1681, 1626 cm$^{-1}$
MS(ISP): 366.4 (M+H$^+$)
Microanalysis: $C_{17}H_{23}N_3O_4S$

|  | C | H | N | S | F |
|---|---|---|---|---|---|
| calc. | 55.87 | 6.34 | 11.50 | 8.77 | 0.00 |
| calc.#) | 54.97 | 6.20 | 11.20 | 8.54 | 1.30 |
| found | 55.38 | 5.89 | 11.34 | 8.49 | 1.69 |

)corr. values for 2.52% $H_2O$, 2.61% $CF_3COOH$ and 0.65 residue (h) (6R,7R)-7-[(Z)-2-(2-Amino-thiazol-4-yl)-2-trityloxyimino-acetylanmino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid In analogy to 1(h), (6R,7R)-7-[(Z)-2-(2-amino-thiazol-4-yl)-2-trityloxyimino-acetylamino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid was synthesized from 1.0 g (2.62 mmol) (E)-(6R,7R)-7-amino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid trifluoroacetate (content of trifluoroacetic acid: 4.25%) and 1.5 g (2.90 mmol) 2-(2-aminothiazol-4-yl)-(Z)-2-trityloxyimino-acetic acid 1-benzotriazole ester.

Yield: 1.41 g (71.6%) white crystals
IR(KBr): 1785, 1683, 1624 cm$^{-1}$
MS(ISP): 777.2 (M+H$^+$)

(i) (6R,7R)-7-[(Z)-2-(2-Amino-thiazol-4-yl)-2-hydroxyimino-acetylamino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid trifluoroacetate Analogously to 1(i), (6R,7R)-7-[(Z)-2-(2-amino-thiazol-4-yl)-2-hydroxyimino-acetylamino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid trifluoroacetate was synthesized by deprotection of 1.41 g (1.80 mmol) (6R,7R) 7-[(Z)-2-(2-amino-thiazol-4-yl)-2-trityloxyimino-acetylamino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid in 11.6 ml (151.5 mmol) trifluoroacetic acid and 0.67 ml (4.17 mmol) of triethylsilane.

Yield: 0.93 g (96.6%) beige crystals
IR(KBr): 1781, 1669, 1633 cm$^{-1}$
MS(ISP): 535.2(M+H$^+$)
Microanalysis: $C_{22}H_{26}N_6O_6S_2$

|  | C | H | N | S | F |
|---|---|---|---|---|---|
| calc. | 49.43 | 4.90 | 15.72 | 11.99 | 0.00 |
| calc.#) | 44.25 | 4.17 | 12.85 | 9.80 | 9.12 |
| found | 44.19 | 4.32 | 12.81 | 9.56 | 9.11 |

)corr. values for 1.39% $H_2O$ and 18.2% $CF_3COOH$ (j) (6R,7R)-7-[(Z)-2-(2-Amino-thiazol-4-yl)-2-cyclopentyloxyimino-acetylamino]-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid In analogy to 1(j), (6R,7R)-7-[(Z)-2-(2-amino-thiazol4-yl)-2-cyclopentyloxyimino-acetylamino]-3-3-[(E)-1-(2,2-dimethyl-propyl)-2-oxo-pyrrolidin-3-ylidenemethyl]-8-oxo-5-thia-1-aza-bicyclo[4.2.0]oct-2-ene-2-carboxylic acid was synthesized by reaction of 1.0 g (2.62 mmol) (E)-(6R,7R)-7 amino-3-[1-(2,2-dimethyl-propyl)-2-oxo-pyrrolidin-3-ylidenemethyl]-8-oxo-5-thia-1-aza-bicyclo[4.2.0]oct-2-ene-2-carboxylic acid trifluoroacetate (content of trifluoroacetic acid: 4.25%) and 1.16 g (2.90 mmol) (Z)-2-(2-amino-thiazol-4-yl)-2-cyclopentyloxyimino-thioacetic acid 5-benzothiazol-2-yl ester.

Yield: 1.28 g (81.0%) beige powder
IR(KBr): 1782, 1679, 1628 cm$^{-1}$
MS(ISP): 603.3 (M+H$^+$)
Microanalysis: $C_{27}H_{34}N_6O_6S_2$

|  | C | H | N | S |
|---|---|---|---|---|
| calc. | 53.81 | 5.69 | 13.94 | 10.64 |
| found#) | 53.17 | 5.39 | 13.65 | 10.40 |

)corr. values with 1.4% $H_2$ and 0.6% residue

EXAMPLE 3

(a) rac-2,4-Dibromo-N-cyclohexylmethyl-butyramide

In analogy to 1(a), rac-2,4-dibromo-N-cyclohexylmethyl-butyramide was synthesized from 4.71 g (41.6 mmol) (aminomethyl)cyclohexane and 10.0 g (37.8 mmol) 2,4-dibromo butanoic acid chloride.

Yield: 11.4 g (90%) beige crystals
IR(KBr): 1786, 1649, 1568 cm$^{-1}$
MS(ISP): 342 (M)

(b) rac-3-Bromo-1-cyclohexylmethyl-pyrrolidine-2-one

In analogy to 1(b), rac-3-bromo-1-cyclohexylmethyl-pyrrolidine-2-one was synthesized by cyclization of 11.4 g (33.4 mmol) rac-2,4-dibromo-N-cyclohexylmethyl-butyramide.

Yield: 8.3 g (85.9%) white crystals
IR(KBr): 2923, 1690 cm$^{-1}$
MS(ISP): 261 (M)

(c) rac-[1-cyclohexylmethyl-2-oxo-pyrolidin-3-yl]-triphenyl-phosphonium bromide

In analogy to 1(c), rac-[1-cyclohexylmethyl-2-oxo-pyrrolidin-3-yl]-triphenyl-phosphonium bromide was synthesized from 8.30 g (31.9 mmol) rac-bromo-1-cyclohexylmethyl-pyrrolidine-2-one and 9.20 g (35.1 mmol) triphenylphosphine.

Yield: 15.3 g (91.6%) white crystals
IR(KBr): 1685, 1437 cm$^{-1}$
MS(ISP): 442.4 (M$^+$)
Microanalysis: $C_{29}H_{33}BrNOP$

|  | C | H | N |
|---|---|---|---|
| calc. | 66.67 | 6.37 | 2.68 |
| found#) | 65.95 | 6.42 | 2.53 |

)corr. values with 1.68% H$_2$O

(d) (E)-(2R,6R,7R)-7-tert-Butoxycarbonylamino-3-[1-cyclohexylmethyl-2-oxo-pyrrolidin-3-ylidenemethyl]-8-oxo-5-thia-1-aza-bicyclo[4.2.0]oct-3-ene-2-carboxylic acid benzhydryl ester In analogy to 1(d), (E)-(2R,6R,7R)-7-tert-butoxycarbonylamino-3-[1-cyclohexylmethyl-2-oxo-pyrrolidin-3-ylidenemethyl]-8-oxo-5-thia-1-aza-bicyclo[4.2.0]oct-3-ene-2-carboxylic acid benzhydryl ester was synthesized from 14.0 g (26.8 mmol) rac-[1-cyclohexylmethyl-2-oxo-pyrrolidin-3-yl]-triphenyl-phosphonium bromide and 11.0 g (22.2 mmol) [6R-(6a,7b)]-7-[[(1,1-dimethylethoxy)carbonyl]amino]-3-formyl-8-oxo-5-thia-1-azabicyclo[4.2.0]oct-3-ene-2-carboxylic acid diphenylmethyl ester.

Yield: 12.5 g (85.4%) yellow foam
IR(KBr): 1783, 1743, 1718 cm$^{-1}$
MS(ISP): 658.4 (M+H$^+$)

(e) (E)-(5R,6R,7R)- and (5S,6R,7R)-7-tert-butoxycarbonylamino-3-[1-cyclohexylmethyl-2-oxo-pyrrolidin-3-ylidenemethyl]-5,8-dioxo-5-thia-1-aza-bicyclo[4.2.0]oct-2-ene-2-carboxylic acid benzhydryl ester In analogy to 1(e), (E)-(5R,6R,7R)- and (5S,6R,7R)-7-tert-butoxycarbonylamino-3-[1-cyclohexylmethyl-2-oxo-pyrrolidin-3-ylidenemethyl]-5,8-dioxo-5-thia-1-aza-bicyclo[4.2.0]oct-3-ene-2-carboxylic acid benzhydryl ester were synthesized from 12.5 g (19.0 mmol) (E)-(2R,6R,7R)-7-tert-butoxycarbonylamino-3-[1-cyclohexylmethyl-2-oxo-pyrrolidin-3-ylidenemethyl]-8-oxo-5-thia-1-aza-bicyclo[4.2.0]oct-3-ene-2-carboxylic acid benzhydryl ester and 4.70 g (19.0 mmol) m-chloroperoxybenzoic acid (70–75%).

Yield: 6.6 g (51.6%) pale yellow foam
IR(KBr): 1797, 1723, 1686 cm$^{-1}$
MS(ISP): 674.3 (M+H$^+$)

(f) (E)-(6R,7R) 7-tert-Butoxycarbonylanino-3-[1-cyclohexylmethyl-2-oxo-pyrrolidin-3-ylidenemethyl]-8-oxo-5-thia-1-aza-bicyclo[4.2.0]oct-2-ene-2-carboxylic acid benzhydryl ester In analogy to 1(f), (E)-(6R,7R)-7-tert-butoxycarbonylamino-3-[1-cyclohexylmethyl-2-oxo-pyrrolidin-3-ylidenemethyl]-8-oxo-5-thia-1-aza-bicyclo[4.2.0]oct-2-ene-2-carboxylic acid benzhydryl ester was synthesized from 6.60 g (9.80 mmol) (E)-(5R,6R,7R)- and (5S,6R,7R)-7-tert-butoxycarbonylamino-3-[1-cyclohexylmethyl-2-oxo-pyrrolidin-3-ylidenemethyl]-5,8-dioxo-5-thia-1-aza-bicyclo[4.2.0]oct-2-ene-2-carboxylic acid benzhydryl ester by reduction with 10.6 g (39.2 mmol) phosphorus tribromide.

Yield: 5.6 g (86.9%) colourless crystals
IR(KBr): 1785, 1719, 1683 cm$^{-1}$
MS(ISP): 658.4 (M+H$^+$)

(g) (E)-(6R,7R)-7-Amino-3-[1-cyclohexylmethyl-2-oxo-pyrrolidin-3-ylidenemethyl]-8-oxo-5-thia-1-aza-bicyclo[4.2.0]oct-2-ene-2-carboxylic acid trifluoroacetate In analogy to 1(g), (E)-(6R,7R)-7-amino-3-[1-cyclohexylmethyl-2-oxo-pyrrolidin-3-ylidenemethyl]-8-oxo-5-thia-1-aza-bicyclo[4.2.0]oct-2-ene-2-carboxylic acid trifluoroacetate was synthesized by deprotection of 5.60 g (8.50 mmol) (E)-(6R,7R)-7-tert-butoxycarbonylamino-3-[1-cyclohexylmethyl-2-oxo-pyrrolidin-3-ylidenemethyl]-8-oxo-5-thia-1-aza-bicyclo[4.2.0]oct-2-ene-2-carboxylic acid benzhydryl ester in 27.4 ml (357.8 mmol) trifluoroacetic acid and 5.5 ml anisole.

Yield: 3.1 g (93.9%) brown crystals
IR(EBr): 2923, 1781, 1680 cm$^{-1}$
MS(ISP): 392.4 (M+H$^+$)
Microanalysis: $C_{19}H_{25}N_3O_4S$

|  | C | H | N | S | F |
|---|---|---|---|---|---|
| calc. | 58.29 | 6.44 | 10.73 | 8.19 | 0.00 |
| calc.#) | 57.09 | 6.26 | 10.39 | 7.92 | 1.62 |
| found | 57.15 | 6.29 | 10.23 | 7.77 | 1.64 |

)calc. values for 0.82% H$_2$O and 3.24% CF$_3$COOH

(h) (6R,7R)-7-[(Z)-2-(2-Amino-thiazol-4-yl)-2-trityloxyimino-acetylanmino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid In analogy to 1(h), (6R,7R)-7-[(Z)-2-(2-amino-thiazol4-yl)-2-trityloxyimino-acetylamino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid was synthesized from 1.0 g (2.43 mmol, content of trifluoroacetic acid: 4.77%) (E)-(6R,7R)-7-amino-3-[1-cyclohexylmethyl-2-oxo-pyrrolidin-3-ylidenemethyl]-8-oxo-5-thia-1-aza-bicyclo[4.2.0]oct-2-ene-2-carboxylic acid trifluoroacetate and 1.48 g (2.70 mmol) 2-(2-aminothiazol-4-yl)-(Z)-2-trityloxyimino-acetic acid 1-benzotriazole ester.

Yield: 0.92 g (47.2%) beige powder
IR(KBr): 1784, 1679, 1625 cm$^{-1}$
MS(ISP): 803.3 (M+H$^+$)

(i) (6R7R)-7-[(Z)-2-(2-Amino-thiazol-4-yl)-2-hydroxyimino-acetylamino]-3-[(E)-1-cyclohexylmethyl-2-oxo-pyrrolidin-3-ylidenemethyl]-8-oxo-5-thia-1-aza-bicyclo[4.2.0]-oct-2-ene-2-carboxylic acid trifluoroacetate Analogously to 1(i), (6R,7R)-7-[(Z)-2-(2-amino-thiazol-4-yl)-2-hydroxyimino-acetylamino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid trifluoroacetate was synthesized by deprotection of 0.87 g (1.08 mmol) (6R,7R)-7-[(Z)-2-(2-amino-thiazol-4-yl)-2-trityloxyimino-acetylamino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid in 6.94 ml (90.6 mmol) trifluoroacetic acid and 0.40 ml (2.49 mmol) triethylsilane.

Yield: 0.54 g (88.9%) beige crystalline powder
IR(KBr): 1779, 1670, 1634 cm$^{-1}$
MS(ISP): 561.2 (M+H$^+$)
Microanalysis: $C_{24}H_{28}N_6O_6S_2$

|       | C     | H    | N     | S     | F    |
|-------|-------|------|-------|-------|------|
| calc. | 51.42 | 5.03 | 14.99 | 11.44 | 0.00 |
| calc.#) | 46.33 | 4.34 | 12.48 | 9.52  | 8.39 |
| found | 46.34 | 4.38 | 12.43 | 9.27  | 8.39 |

)calc. values for 1.84% H$_2$O and 16.8% CF$_3$COOH

(j) (6R,7R)-7-[(Z)-2-(2-Amino-thiazol-4-yl)-2-cyclopentyloxyimino-acetylamino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid Analogously to 1(j), (6R,7R)-7-[(Z)-2-(2-amino-thiazol-4-yl)-2-cyclopentyloxyimino-acetylamino]-3-[(E)-1-cyclohexylmethyl-2-oxo-pyrrolidin-3-ylidenemethyl]-8-oxo-5-thia-1-aza-bicyclo[4.2.0]oct-2-ene-2-carboxylic acid was synthesized by reaction of 1.0 g (2.43 mmol; content of trifluoroacetic acid 4.77%) (E)-(6R,7R)-7-amino-3-[1-cyclohexylmethyl-2-oxo-pyrrolidin-3-ylidenemethyl]-8-oxo-5-thia-1-aza-bicyclo[4.2.0]oct-2-ene-2-carboxylic acid trifluoroacetate and 1.08 g (2.70 mmol) (Z)-2-(2-amino-thiazol-4-yl)-2-cyclopentyloxyimino-thioacetic acid 5-benzothiazol-2-yl ester.

Yield: 1.26 g (78.7%) light brown powder
IR(KBr): 1780, 1674, 1629 cm$^{-1}$
MS(ISP): 629.4 (M+H$^+$)

|       | C     | H    | N     | S     |
|-------|-------|------|-------|-------|
| calc. | 55.40 | 5.77 | 13.37 | 10.20 |
| found#) | 54.47 | 5.69 | 13.09 | 10.12 |

)corr. values with 1.52% H$_2$O

We claim:
1. A compound of formula I

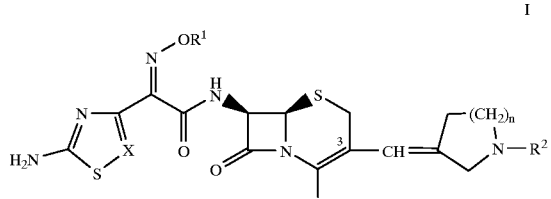

wherein
 R$^1$ is hydrogen, lower alkyl, aralkyl, cycloalkyl, R$^3$CO— or —C(R$^4$R$^5$)CO$_2$R$^6$; where R$^4$ and R$^5$ are each independently hydrogen or lower alkyl, or R$^4$ and R$^5$ taken together with the carbon atom to which they are attached form a cycloalkyl group; R$^3$ is hydrogen or lower alkyl and R$^6$ is hydrogen, lower alkyl, lower alkenyl or other carboxylic acid protecting group;
 R$^2$ is isobutyl;
 n is 0, 1 or 2;
 X is CH or N;
as well as readily hydrolyzable esters thereof selected from the group lower alkanoyloxy-alkyl, lower alkoxycarbonyloxyalkyl, lactonyl, lower alkoxymethyl, benzyl, cyanomethyl, (2,2-dimethyl-1-oxopropoxy)methyl, 2-[(-methylpropoxy)carbonyl]-2-pentenyl, 1-[[(1-methylethoxy)carbonyl]oxy]ethyl, 1-(acetyloxy)ethyl, (5-methyl-2-oxo-1,3-dioxol-4-yl)methyl, 1-[[(cyclohexyloxy)carbonyl]oxy]ethyl, and 3,3-dimethyl-2-oxobutyl esters, pharmaceutically acceptable salts of said compounds and hydrates of the compounds of formula I and of their esters and salts.

2. Compounds of claim 1, wherein R$^1$ is hydrogen and n is 1.

3. A compound of formula II

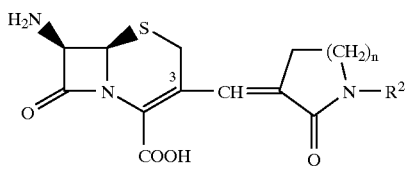

wherein
 R$^2$ is isobutyl; and
 n is 0, 1 or 2;
or esters thereof selected from the group silyl, benhydryl, lower alkanoyloxy-alkyl, lower alkoxycarbonyloxyalkyl, lactonyl, lower alkoxymethyl, benzyl, cyanomethyl, (2,2-dimethyl-1-oxopropoxy)methyl, 2-[(-methylpropoxy)carbonyl]-2-pentenyl, 1-[[(1-methylethoxy)carbonyl]oxy]ethyl, 1-(acetyloxy)ethyl, (5-methyl-2-oxo-1,3-dioxol-4-yl)methyl, 1-[[(cyclohexyloxy)carbonyl]oxy]ethyl, and 3,3-dimethyl-2-oxobutyl esters or salts thereof.

4. A compound of formula IIA

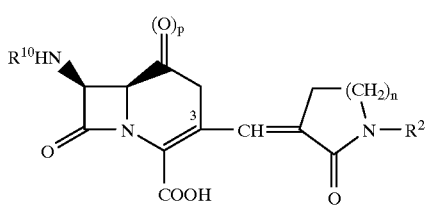

wherein
 R$^2$ is isobutyl;
 p is 0 or 1;
 n is 0, 1, or 2; and
 R$^{10}$ is an amino protecting group,
or esters thereof selected from the group silyl, benhydryl, lower alkanoyloxy-alkyl, lower alkoxycarbonyloxyalkyl, lactonyl, lower alkoxymethyl, benzyl, cyanomethyl, (2,2-dimethyl-1-oxopropoxy)methyl, 2-[(-methylpropoxy)carbonyl]-2-pentenyl, 1-[[(1-methylethoxy)carbonyl]oxy]ethyl, 1-(acetyloxy)ethyl, (5-methyl-2-oxo-1,3-dioxol-4-yl)methyl, 1-[[(cyclohexyloxy)carbonyl]oxy]ethyl, and 3,3-dimethyl-2-oxobutyl esters or salts thereof.

5. A pharmaceutical composition comprising a pharmacologically effective amount of a compound of formula I

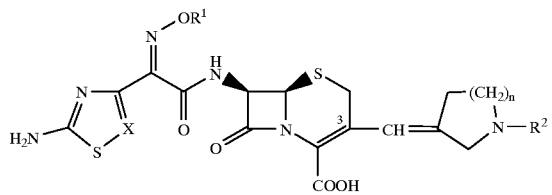

wherein
- R¹ is hydrogen, lower alkyl, aralkyl, cycloalkyl, R³CO— or —C(R⁴R⁵)CO₂R⁶; where R⁴ and R⁵ are each independently hydrogen or lower alkyl, or R⁴ and R⁵ taken together with the carbon atom to which they are attached form a cycloalkyl group; R³ is hydrogen or lower alkyl and R⁶ is hydrogen, lower alkyl, lower alkenyl or other carboxylic acid protecting group;
- R² is isobutyl;
- n is 0, 1 or 2;
- X is CH or N;

as well as readily hydrolyzable esters thereof selected from the group lower alkanoyloxy-alkyl, lower alkoxycarbonyloxyalkyl, lactonyl, lower alkoxymethyl, benzyl, cyanomethyl, (2,2-dimethyl-1-oxopropoxy)methyl, 2-[(-methylpropoxy)carbonyl]-2-pentenyl, 1-[[(1-methylethoxy)carbonyl]oxy]ethyl, 1-(acetyloxy)ethyl, (5-methyl-2-oxo-1,3-dioxol-4-yl)methyl, 1-[[(cyclohexyloxy)carbonyl]oxy]ethyl, and 3,3-dimethyl-2-oxobutyl esters, pharmaceutically acceptable salts of said compounds and hydrates of the compounds of formula I and of their esters and salts, and a therapeutically inert carrier.

6. Compounds of claim 1 with the 3-substituent in the E-form, viz. having the formula

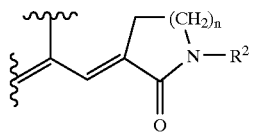

7. A method of treating bacterial infection in a mammal comprising administering to said mammal a compound of formula I

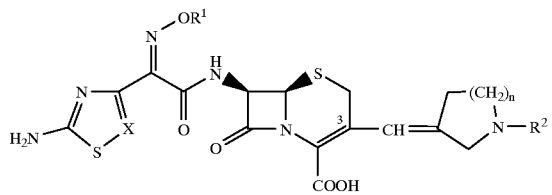

wherein
- R¹ is hydrogen, lower alkyl, aralkyl, cycloalkyl, R³CO— or —C(R⁴R⁵)CO₂R⁶; where R⁴ and R⁵ are each independently hydrogen or lower alkyl, or R⁴ and R⁵ taken together with the carbon atom to which they are attached form a cycloalkyl group; R³ is hydrogen or lower alkyl and R6 is hydrogen, lower alkyl, lower alkenyl or other carboxylic acid protecting group;
- R² is isobutyl;
- n is 0, 1 or 2;
- X is CH or N;

as well as readily hydrolyzable esters thereof selected from the group lower alkanoyloxy-alkyl, lower alkoxycarbonyloxyalkyl, lactonyl, lower alkoxymethyl, benzyl, cyanomethyl, (2,2-dimethyl-1-oxopropoxy)methyl, 2-[(-methylpropoxy)carbonyl]-2-pentenyl, 1-[[(1-methylethoxy)carbonyl]oxy]ethyl, 1-(acetyloxy)ethyl, (5-methyl-2-oxo-1,3-dioxol-4-yl)methyl, 1-[[(cyclohexyloxy)carbonyl]oxy]ethyl, and 3,3-dimethyl-2-oxobutyl esters, pharmaceutically acceptable salts of said compounds and hydrates of the compounds of formula I and of their esters and salts, and a therapeutically inert carrier, in an amount which is effective in treating bacterial infections.

8. The compound of claim 2,

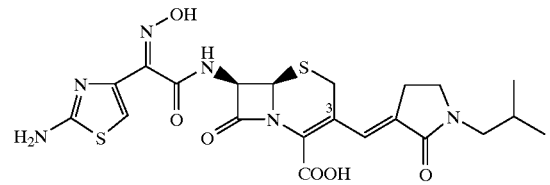

(6R,7R)-7-[(Z)-2-(2-amino-thiazol-4-yl)-2-hydroxyiminoacetylamino]-3-[(E)-1-isobutyl-2-oxo-pyrrolidin-3-ylidenemethyl]-8-oxo-5-thia-1-azabicyclo[4.2.0]oct-2-ene-2-carboxylic acid.

9. The composition of claim 5, wherein the compound is

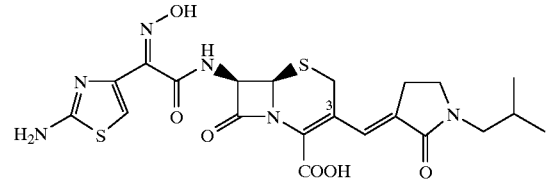

(6R, 7R)-7-[(Z)-2-(2-amino-thiazol-4-yl)-2-hydroxyiminoacetylamino]-3-[(E)-1-isobutyl-2-oxo-pyrrolidin-3-ylidenemethyl]-8-oxo-5-thia-1-azabicyclo[4.2.0]oct-2-ene-2-carboxylic acid.

10. The method of claim 7, wherein the compound is

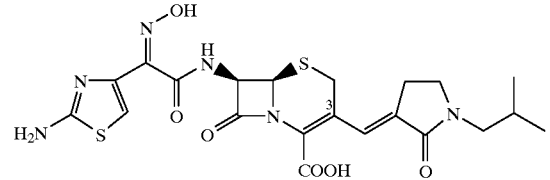

(6R,7R)-7-[(Z)-2-(2-amino-thiazol-4-yl)-2-hydroxyiminoacetylamino]-3-[(E)-1-isobutyl-2-oxo-pyrrolidin-3-ylidenemethyl]-8-oxo-5-thia-1-azabicyclo[4.2.0]oct-2-ene-2-carboxylic acid.

* * * * *

UNITED STATES PATENT AND TRADEMARK OFFICE
CERTIFICATE OF CORRECTION

PATENT NO. : 5,925,632
DATED : July 20, 1999
INVENTOR(S) : Ingrid Heinze-Krauss and Hans Richter It is certified that error appears in the above-indentified patent and that said Letters Patent is hereby corrected as shown below:

On the title page, item [54] and column 1, line 2:

In the Title

Delete "CEPHALSPORINES" and insert -- CEPHALOSPORINES --.

In the Claims

In claim 1, column 23, lines 45-54;

claim 5, column 25, lines 1-10; and claim 7, column 25, lines 50-58 please delete "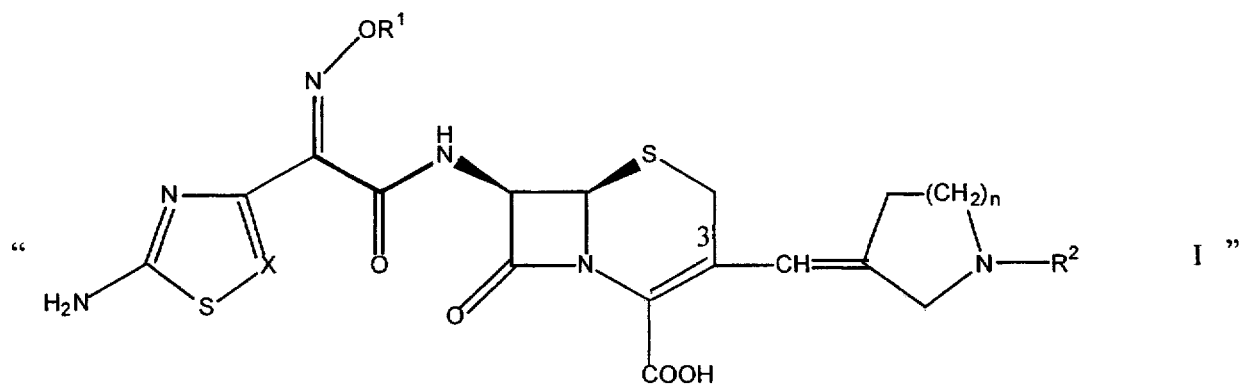 I"

UNITED STATES PATENT AND TRADEMARK OFFICE
CERTIFICATE OF CORRECTION

PATENT NO. : 5,925,632
DATED : July 20, 1999
INVENTOR(S) : Ingrid Heinze-Krauss and Hans Richter It is certified that error appears in the above-indentified patent and that said Letters Patent is hereby corrected as shown below:

and insert

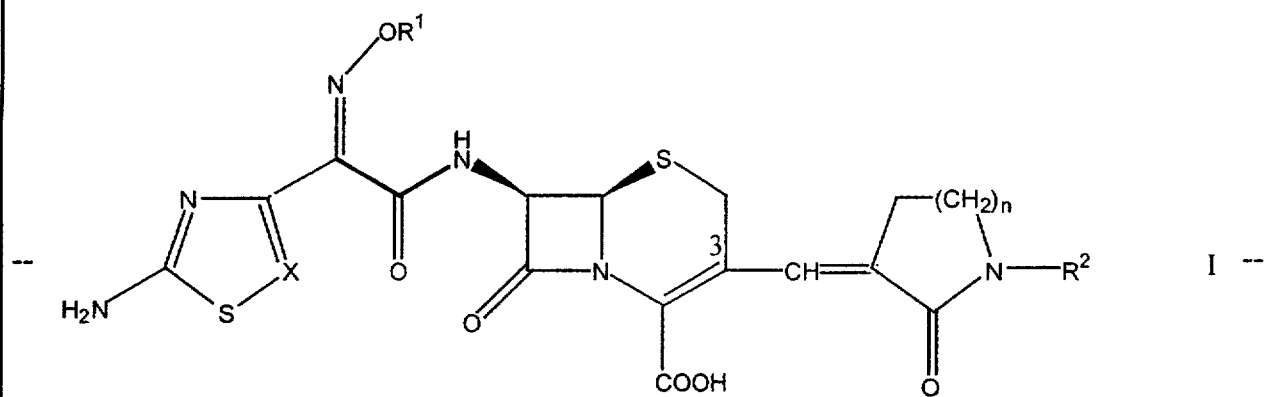

-- I --

UNITED STATES PATENT AND TRADEMARK OFFICE
CERTIFICATE OF CORRECTION

PATENT NO. : 5,925,632
DATED : July 20, 1999
INVENTOR(S) : Ingrid Heinze-Krauss and Hans Richter It is certified that error appears in the above-identified patent and that said Letters Patent is hereby corrected as shown below:

In claim 2, column 24, line 11 and claim 6, column 25, line 35 please delete "Compounds" and insert -- The compound --.

In claim 7, column 26, line 1, please delete "R6" and insert -- $R^6$ --.

Signed and Sealed this

Twenty-second Day of February, 2000

Attest:

Q. TODD DICKINSON

Attesting Officer

Commissioner of Patents and Trademarks